(12) United States Patent
Aubanel

(10) Patent No.: US 7,277,164 B2
(45) Date of Patent: Oct. 2, 2007

(54) PROCESS AND STATION FOR INSPECTING THE PAINTING OF MOTOR VEHICLE BODYWORK PARTS

(75) Inventor: Laurent Aubanel, Villette sur Ain (FR)

(73) Assignee: Compagnie Plastic Omnium (FR)

( * ) Notice: Subject to any disclaimer, the term of this patent is extended or adjusted under 35 U.S.C. 154(b) by 12 days.

(21) Appl. No.: 11/184,256

(22) Filed: Jul. 18, 2005

(65) Prior Publication Data
US 2006/0092408 A1 May 4, 2006

(30) Foreign Application Priority Data
Jul. 19, 2004 (FR) .................................. 04 07985

(51) Int. Cl.
*G01N 21/88* (2006.01)
(52) U.S. Cl. .................... 356/237.2; 356/445; 356/237
(58) Field of Classification Search ................ 356/237, 356/237.1–237.3, 371; 250/562, 219, 572
See application file for complete search history.

(56) References Cited

U.S. PATENT DOCUMENTS

| | | | |
|---|---|---|---|
| 3,513,320 A * | 5/1970 | Weldon ....................... 250/548 |
| 4,715,709 A | 12/1987 | Sekine et al. |
| 4,853,879 A | 8/1989 | Matzoll, Jr. et al. |
| 5,237,404 A | 8/1993 | Tanaka et al. |
| 5,572,324 A * | 11/1996 | Ventura ....................... 356/613 |
| 5,773,840 A | 6/1998 | Pryor et al. |

FOREIGN PATENT DOCUMENTS

| | | |
|---|---|---|
| EP | 1076221 A2 | 2/2001 |
| EP | 1429114 A2 | 6/2004 |
| WO | WO87/00629 | 1/1987 |

* cited by examiner

*Primary Examiner*—Gregory J. Toatley, Jr.
*Assistant Examiner*—Rebecca C. Slomski
(74) *Attorney, Agent, or Firm*—Robert L. Epstein; Epstein Drangel Bazerman & James, LLP

(57) ABSTRACT

A method for inspecting the painting of bodywork parts using an optical measurement instrument that is moved parallel to the parts being inspected. An inspection station for implementing the method.

4 Claims, 1 Drawing Sheet

PROCESS AND STATION FOR INSPECTING THE PAINTING OF MOTOR VEHICLE BODYWORK PARTS

The present invention relates to a process and a station for inspecting the painting of motor vehicle bodywork parts.

BACKGROUND OF THE INVENTION

It is known that bodywork parts that are painted off the main assembly line for a vehicle need to be painted in compliance with precise criteria in terms of color and surface state so that said parts present the same appearance as the remainder of the bodywork which is painted as a whole.

It is also known that the settings of a painting line can drift as a function of various factors, such as, for example: humidity, ambient temperature, and atmospheric pressure, and that it is essential to monitor parts on leaving the painting line, at least to inspect their quality, and possibly also to adjust the settings of the painting line accordingly.

To this end, it is known to use an optical measuring instrument such as that sold under the reference Carflash by the American supplier X-Rite.

That instrument is installed at the end of a painting line on a stop-and-go station, i.e. a station in front of which parts under inspection are stopped, with measurements being performed while they are stationary, after which they continue moving along the line.

Until now, stations for inspecting the painting of motor vehicle bodywork parts have always been of the stop-and-go type since the measurement instrument is known to be highly sensitive to vibration, and any movement of parts along the line inevitably leads to high levels of vibration in the parts.

Indeed, the manufacturer recommends that the measurement instrument be used in that way.

Their drawback is particularly severe insofar as it applies to painting lines in which bodywork parts are carried individually by trays or masts, moving on a conveyor, and their low weight does not give them sufficient inertia to absorb vibration from the conveyor.

Things are different on a line for painting unpainted "bodies-in-white" of vehicles, since they are heavy enough to limit considerably the effects of conveyor vibration.

OBJECTS AND SUMMARY OF THE INVENTION

Thus, the problem the invention seeks to solve relates to painting lines other than lines for painting bodies-in-white, and for which there exists a prejudice to the effect that a measurement instrument cannot be used to monitor parts that are moving.

Going against this prejudice, the inventor has undertaken measurement tests on moving parts and has found that by positioning the instrument on a robot that tracks the moving parts in conventional manner, such as the robots of the kind used for painting moving parts, measurement results can be obtained that are sufficiently reliable to identify color drift.

Thus, the present invention provides a process for inspecting the painting of motor vehicle bodywork parts at the outlet from a painting line other than a painting line for bodies-in-white, the process consisting in presenting an optical measurement instrument to a part at the outlet from the painting line, wherein the instrument is moved along the path of the moving part while the measurement is being performed, in such a manner that during a predetermined time interval the instrument and the part are substantially stationary relative to each other.

In the invention, the term "substantially stationary relative to each other" is used to mean that the instrument and the part are traveling at the same speed along two parallel paths, with any vibration to which the part might be subjected not being taken into consideration when assessing this criterion of being substantially stationary.

The present invention also provides a station for inspecting the painting of motor vehicle bodywork parts, the station including an optical measurement instrument mounted on a tracking robot suitable for moving along the path of a moving part during measurement, in such a manner that during a predetermined time interval, the instrument and the part are substantially stationary relative to each other.

Advantageously, the tracking robot is of the same type as the robot used for painting moving parts.

According to other characteristics of the invention that are advantageous but optional, and that can be taken singly or in combination:

the measurement instrument is suitable for measuring along at least two angles, and preferably along three to five angles; and the measurement instrument is suitable for delivering a measurement characteristic of the hue, the leveling, the pinpoint blistering, and/or the brilliance of the painting.

BRIEF DESCRIPTION OF THE DRAWINGS

In order to make the invention better understood, there follows a description of an embodiment given by way of an example that does not limit the scope of the invention, and described with reference to the accompanying drawing, in which.

MORE DETAILED DESCRIPTION

Figure 1:
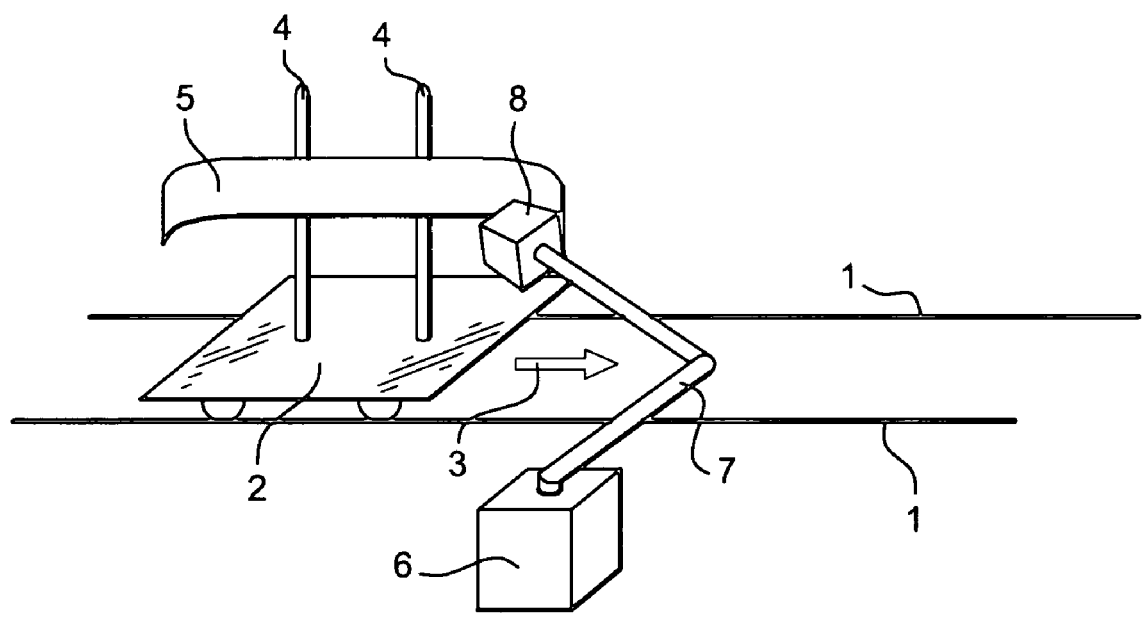
FIG. 1 is a perspective view of a station for inspecting painting at the outlet from a painting line.

The inspection station shown in the drawing is located at the outlet from a painting line for painting parts other than bodies-in-white.

The drawing shows a conveyor having rails 1 supporting a carriage 2 having two masts 4 together carrying a bodywork part 5 of painted plastics material, and specifically, in this example, a bumper shield.

The shield 5 is carried individually and its light weight makes it sensitive to the vibration of the carriage traveling along the rails 1 in the direction indicated by arrow 3.

Beside the rails 1, a robot 6 carries a measuring instrument 8 on the end of a manipulator arm 7.

The manipulator arm 7 is programmed by a control device (not shown) for the robot so as to move in such a manner as to impart movement in translation to the measurement instrument 8 that is identical to the movement in translation of the bodywork part 5 over a predetermined time interval of duration that is sufficient to take at least one measurement.

During this time interval, the measurement instrument and the shield 5 are considered as being stationary relative to each other, ignoring the vibration of the shield.

The robot 6 is of the same type as those used on the painting line, and the instrument 8 is constituted, for example, by the Carflash instrument from the American supplier X-Rite.

Figure 2:
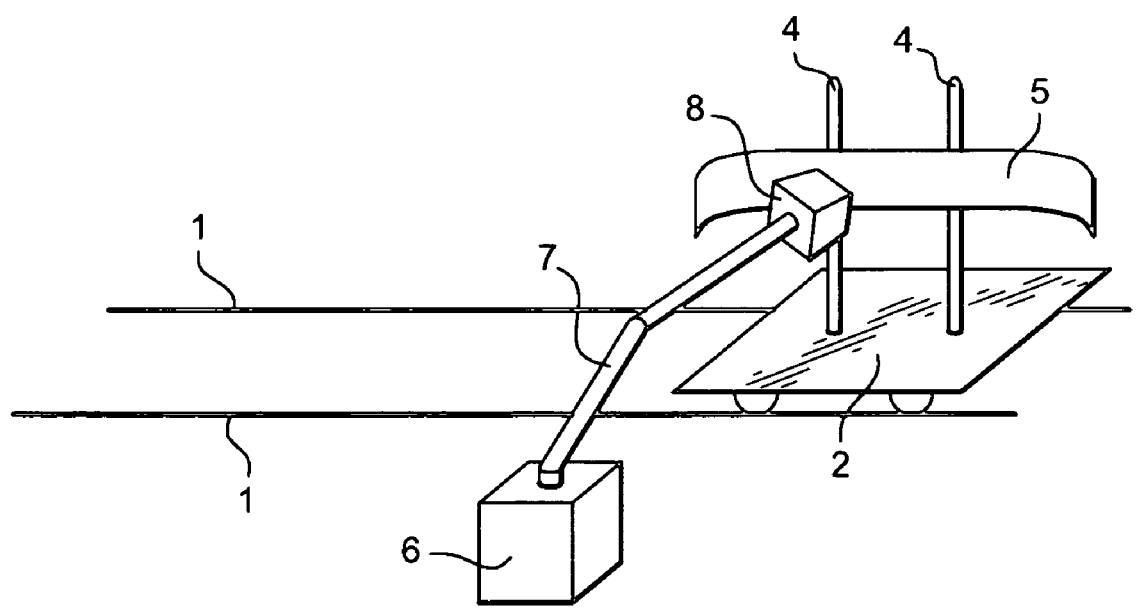
FIG. 2 is a view analogous to FIG. 1 showing a later stage in the inspection process.

In FIG. 2, it can be seen that with the carriage moving along arrow 3, each time the robot is taking a measurement, it tracks the path of the carriage so as to keep the measurement instrument 8 stationary relative to the shield 5.

The measurements provided by the measurement instrument 8 are then used in a device (not shown) for assessing the paint quality of the shield.

Naturally, the embodiment described above is not limiting in any way and could be modified in any desirable manner without thereby going beyond the ambit of the invention.

What is claimed is:

1. A process for inspecting the painting of motor vehicle bodywork parts at the outlet from a painting line other than a painting line for bodies-in-white, the bodywork parts moving along a path during inspection, the process consisting in presenting an optical measurement instrument to a part at the outlet from the painting line, wherein the instrument is moved along the path of the moving part while the measurement is being performed, in such a manner that during a predetermined time interval the instrument and the part are substantially stationary relative to each other, the predetermined time interval being sufficient to take at least one measurement of the painting.

2. A station for inspecting the painting of motor vehicle bodywork parts, the bodywork parts moving along a path during the inspection, the station including an optical measurement instrument mounted on a tracking robot suitable for moving along the path of a moving part during measurement, in such a manner that during a predetermined time interval, the instrument and the part are substantially stationary relative to each other, the predetermined time interval being sufficient to take at least one measurement of the painting.

3. A station according to claim 2, in which the measurement instrument is suitable for measuring along at least two angles, and preferably along three to five angles.

4. A station according to claim 2, in which the measurement instrument is suitable for delivering a measurement characteristic of the hue, the leveling, the pinpoint blistering, and/or the brilliance of the painting.

* * * * *